United States Patent [19]

Nichols

[11] Patent Number: 5,209,923
[45] Date of Patent: May 11, 1993

[54] SUNSCREEN COMPOSITION
[75] Inventor: Larry D. Nichols, Arlington, Mass.
[73] Assignee: Moleculon, Inc., Elizabeth, N.J.
[21] Appl. No.: 869,105
[22] Filed: Apr. 14, 1992

Related U.S. Application Data

[63] Continuation of Ser. No. 619,737, Nov. 29, 1990, abandoned, which is a continuation-in-part of Ser. No. 358,690, May 30, 1989, Pat. No. 5,000,947.

[51] Int. Cl.$^5$ .......................... A61K 7/42; A61K 9/14
[52] U.S. Cl. ...................................... 424/59; 424/60; 424/69; 424/488; 424/489; 424/499; 424/DIG. 5; 424/401; 428/402.2; 514/781; 514/844; 514/951
[58] Field of Search ................ 424/401, 59, 60, 69, 424/488, 489

[56] References Cited

U.S. PATENT DOCUMENTS

| | | | |
|---|---|---|---|
| 3,824,085 | 7/1974 | Teng et al. | 44/7 B |
| 3,846,404 | 11/1974 | Nichols | 260/230 |
| 3,940,384 | 2/1976 | Teng et al. | 260/226 |
| 3,985,298 | 10/1976 | Nichols | 239/54 |
| 4,016,254 | 4/1977 | Seager | 424/33 |
| 4,024,073 | 5/1977 | Shimizu et al. | 252/316 |
| 4,029,726 | 6/1977 | Nichols | 264/41 |
| 4,067,824 | 1/1978 | Teng et al. | 252/522 |
| 4,128,507 | 12/1978 | Mitzner | 252/522 |
| 4,193,989 | 3/1980 | Teng et al. | 424/60 |
| 4,369,173 | 1/1983 | Causland et al. | 424/35 |
| 4,383,988 | 5/1983 | Teng et al. | 424/68 |
| 4,597,960 | 7/1986 | Cohen | 424/28 |
| 4,643,856 | 2/1987 | Nichols | 264/41 |
| 4,690,786 | 9/1987 | Ninomiya et al. | 264/4.6 |
| 4,690,825 | 9/1987 | Won | 424/501 |
| 4,695,464 | 9/1987 | Aldermann | 424/449 |
| 4,708,821 | 11/1987 | Shimokawa et al. | 512/12 |
| 4,724,240 | 2/1988 | Abrutyn | 514/847 |
| 4,738,851 | 4/1988 | Schoenwald et al. | 424/488 |
| 4,752,496 | 6/1988 | Fellows et al. | 427/27 |
| 4,755,433 | 7/1988 | Patel et al. | 428/422 |
| 4,888,420 | 12/1989 | Steiner et al. | 536/64 |
| 4,925,667 | 5/1990 | Fellows et al. | 424/401 |
| 4,940,588 | 7/1990 | Sparks et al. | 424/490 |
| 4,952,402 | 8/1990 | Sparks et al. | 424/419 |
| 5,000,947 | 3/1991 | Nichols | 424/69 |
| 5,013,473 | 5/1991 | Norbury et al. | 252/174 |

OTHER PUBLICATIONS

Moleculon, Inc., Form 10-K for FY ended Nov. 30, 1988, pp. 1-7.

Primary Examiner—Thurman K. Page
Assistant Examiner—James M. Spear
Attorney, Agent, or Firm—Thomas J. Engellenner; James E. Maslow

[57] ABSTRACT

Liquefiable powder compositions are disclosed for the delivery of topical sunscreens. In particular, microporous cellulosic powders, such as cellulose acetates or nitrates, are disclosed as high liquid content vehicles for the delivery of liquid sunscreen preparations dissolved or dispersed in a liquid carrier. The resulting powders permit the application of the sunscreen preparation by simply rubbing or otherwise applying the formulation onto the skin in such a manner that the powder liquefies and appears to vanish. Upon application, the frangible liquid loaded cellulosic powders break up into minute particles that adhere well to the skin and do not pass easily beyond the initial layers of the skin, but do permit the slow release of the sunscreen agent.

6 Claims, No Drawings

SUNSCREEN COMPOSITION

REFERENCE TO RELATED APPLICATION

This application is a continuation of application Ser. No. 619,737, filed Nov. 29, 1990 now abandoned, which is a continuation-in-part of U.S. Ser. No. 358,690 filed May 30, 1989, now U.S. Pat. No. 5,000,947.

BACKGROUND OF THE INVENTION

The technical field of this invention is the topical application of personal care agents and, in Particular, methods and compositions for topical application of sunscreens.

In recent years, the public has become increasingly aware of the harmful effects of overexposure to the sun, Particularly the ultraviolet components of sunlight. Painful sunburn is a common result of short-term overexposure. Additionally, wrinkling and premature aging of the skin, and even cancer, can result from chronic overexposure.

Sunscreens typically operate by absorbing ultraviolet radiation. Compositions useful as sunscreens should disperse easily onto the skin, closely adhere to the skin, resist penetration through the skin, and resist shedding by perspiration or by immersion in fresh or salt water.

Unfortunately, most sunscreens do not fully satisfy these requirements in terms of durability and efficacy. Often, sunscreen compositions are quickly shed from the skin or absorbed into the lower layers of the skin where their radiation blocking activity is markedly reduced.

There exists a need for better sunscreen compositions, particularly for economical, long-term Protection from the harmful effects of ultraviolet radiation.

SUMMARY OF THE INVENTION

Liquefiable powder compositions are disclosed for the delivery of topical sunscreens. In particular, microporous cellulosic powders, such as cellulose acetates or nitrates, are disclosed as high-liquid content vehicles for the delivery of sunscreen preparations dissolved or dispersed in a liquid carrier. The resulting powders permit the application of the sunscreen preparation by simply rubbing, or otherwise applying, the composition to the skin in such a manner that the powder liquefies and appears to vanish. Upon application, the frangible liquid-loaded, cellulosic powders break up into minute particles that adhere well to the skin and do not pass easily beyond the initial layers of the skin, but do permit the slow release of the sunscreen agent.

Details of the formation of cellulosic powders can be found in the above-referenced parent application, U.S. Ser. No. 358,690, filed May 30, 1989, now U.S. Pat. No. 5,000,947 and a commonly-owned, copending application entitled "Process For Producing Liquid-Loaded Powders", by Larry D. Nichols and John F. Cline, filed contemporaneously herewith, both of which are incorporated herein by reference. A preferred polymer liquid-loadable powder includes microporous cellulose triacetate prepared by the method of the above application, Attorney Docket No. MOE-014, entitled "Process For Producing Liquid-Loaded Powders".

In one technique, the liquefiable powders are formed by dissolving a cellulosic polymer and a pore-forming liquid in a volatile, polar solvent (e.g., a low molecular weight halogenated hydrocarbon, ester or diester) and then dispersively evaporating the solution, for example, by spray drying. Suitable volatile solvents for cellulosic polymers include methylene chloride, acetone, ethyl acetate, ethyl carbonate, methyl formate and the like. Methylene chloride is a preferred solvent when the cellulosic polymer is cellulose triacetate. Alternatively, other solvents, such as formic acid or the like, can be used and the resulting solution can be sprayed into a non-solvent such as methanol where the powder particles are then recovered by filtration and rinsing. The active agent can be incorporated into the solvent or introduced by liquid phase substitution after the powder is formed.

The cellulosic powders useful in the present invention can range from about one to about 500 micrometers in average diameter, preferably from about 5 to about 100 micrometers in average diameter, and typically are roughly microspherical in shape. They are further characterized by being microporous with interconnecting pores ranging in size from about one to about 500 nanometers or greater and are capable of holding liquid payloads of active agents. The cellulosic powder can be formed from cellulosic polymers chosen from the group of cellulose acetates, cellulose butyrates, cellulose nitrates, cellulose propionates, ethyl celluloses and discrete or molecular mixtures thereof. One preferred cellulosic powder is a polymeric powder of cellulose triacetate, having a (dry) acetyl content greater than about 42 percent. The liquid content of the cellulosic powders of the present invention can range from about 50 percent to about 95 percent by weight.

Compositions made in accordance with the present invention permit the delivery of effective concentrations of active sunscreen ingredients without many of the problems normally associated with liquids and oils. By assisting in the distribution of sunscreen agents uniformly over the skin and retarding the penetration of the sunscreen agents into the lower layers of the skin, the compositions of the invention enhance efficacy, improve economy and reduce the risk of adverse reactions.

Sunscreens which can be used in the practice of the invention include oxybenzone, amyl-p-dimethylaminobenzoate, homomethyl salicylate, octyl salicylate, mono-p-aminobenzoate, octyl-methoxycinnamate, 2-ethoxy ethyl-p-methoxycinnamate as well as derivatives and mixtures thereof. Such sunscreens can be formulated as solutions or dispersions in oils, such as mineral oil or silicone oil, or in emollients, such as isopropyl myristates or palmitates, with or without additional volatile solvents, such as ethanol, isopropyl alcohol or other alcohols.

In one embodiment, the sunscreen agent can be incorporated into frangible, cellulosic microbeads or other powder forms and then formulated into a cream or emulsion type vehicle by mixture with a liquid base. Alternatively, the compositions can be formulated as loose powders, compacted into cakes, or blended with binders, and shaped into bars or application sticks.

Suitable liquid bases for cream or lotion type embodiments include water, oils and moisturizing agents, such as glycerin or aloe vera gels. Additional ingredients can include stearic acid, silicone liquids, triethanolamine, petrolatum, cetyl alcohol, carbomers, and the like.

In the compacted cake embodiments, the liquid loaded powders can be compacted to packing densities ranging from about 55 percent to about 75 percent, more preferably from about 60 percent to about 70 percent of the void-free density of the combined materials to yield cakes that are dry and firm and yet readily permit transfer of the formulation to the skin by finger or brush.

Such compacted cakes can be obtained by applying a pressure ranging from about 50 to about 80 PSI to a cellulosic powder which has been appropriately loaded with a liquid payload of the active agent. In the absence of other additives, the resulting shaped articles have a compacted density ranging from about 0.55 to about 0.75 gm/cc.

Sticks or bars incorporating liquefiable powders with active agent payloads can be made by a variety of techniques. For example, sticks can be formulated by compounding a liquefiable powder with fatty alcohols, fatty acids, and/or salts of fatty acid anions with metallic or alkanolamine cations to produce a stick having a soap as the binding agent.

Alternatively, stick compositions can be formed by compounding a liquefiable powder with soft, water-soluble polymers, such as polyethylene glycols or polypropylene glycols, to produce a stick having a soluble wax as the binding agent. Sticks can also be made up by compounding a liquefiable powder with silicones or with blends of liquids and solids, such as salts and/or propylene glycols, to produce sticks having a thick or partially-solidified slurry as the binding agent. In yet another approach, sticks can be formed by compounding a liquefiable powder with a fusible wax, including fatty esters, silicone waxes, polyglycol waxes and aliphatic waxes, and then applying heat and pressure to produce sticks having a wax as the binding agent.

The above binding agents can be introduced directly, or as payload in a second portion of liquefiable powder to be blended with that carrying the active ingredient. Other methods of stick production will readily occur to those skilled in the art.

Regardless of the embodiment, various additives can be mixed with the liquid-loaded Particles (or liquid base) including, for example, talc, cornstarch, waxes, silicones, analgesics, cosmetics, fragrances, lubricants, emollients, moisturizers, medications and other personal care agents, colorants, pearlescent agents, and mixtures of such additives.

The invention will next be described in connection with certain exemplary methods and compositions. However, it should be clear that various additions, subtractions and changes can be made by those skilled in the art without departing from the spirit or scope of the invention. For example, various additives can be mixed together with the sunscreen loaded powder particles of the invention, including, for example, talc, cornstarch, waxes, silicones, cosmetics, fragrances, lubricants, emollients, moisturizers, medications and other personal care agents, as well as colorants, pearlescent agents, and mixtures of such additives.

In some applications, it may also be preferable to include a quantity of a dry cellulosic Powder (e.g., less than 50 percent of the total cellulosic components) to provide additional structural integrity to the composition. The term "dry cellulosic powder" is used herein to describe powders whose internal pores are liquid-free or have a liquid content of less than 50 percent.

DETAILED DESCRIPTION

The examples below illustrate the preparation of liquefiable sunscreen loaded powders.

EXAMPLE 1

A liquefiable powder was prepared by spray evaporative drying. A liquid porogen solution was prepared from 8.15 parts by weight of Parsol MCX (octyl methoxycinnamate, Givaudan Corporation, Clifton, N.J.), 5.45 parts of Sunarome WMD (octyl salicylate, Felton International, Inc., Brooklyn, N.Y.) and 8.5 parts of Dow Corning 55E silicone fluid. 34.79 parts of CTA and 400 parts of said porogen were then dissolved in 3478.21 parts of methylene chloride by moderate stirring for 4 hours. This solution was sprayed at 1000 PSI from a 0.0135" nozzle downward into a tower 100 cm in diameter and 300 cm tall through which 1250 liters per minute of solvent-free air was passing from top to bottom.

The resulting evaporatively-formed, liquid-containing cellulose triacetate powder was collected on a fabric filter spanning the bottom of the tower, and the solvent-laden air was passed through carbon beds to collect solvent vapors.

The product was transferred from the filter into a steel tray and left exposed as a 1 cm layer in a ventilated hood for 15 minutes to remove residual solvent. Analysis showed 12.7 percent sunscreen formulation, 79.3 percent silicone fluid, and 8.0 percent cellulose triacetate, with less than ppm of methylene chloride.

EXAMPLE 2

35 gr of CTA was dissolved in 465.2 gr methylene chloride. A mixture of 32.6 gr Parsol MCX, 21.8 gr Sunarome WMO, and 340.0 gr phenyltrimethicone (an occlusive-type moisturizing agent which prevents moisture from leaving the skin surface) were dissolved in 3016 gr methylene chloride, and then the two solutions were mixed. The resulting lacquer was sprayed at 1175 psi from a 0.0135 inch diameter, single fluid pressure/pneumatic nozzle downwardly into a tower through which 55 cfm air was passing from top to bottom. Nozzle diameter was 0.0135 inch. The temperature at the top of the tower measured 30.5° C. and the base at 17.3° C., with a relative humidity of about 40 to 60 percent or less. Mean particle size was 38.1 microns with 90% less than 78.9 microns.

EXAMPLE 3

200 gr of commercial suntan oil (sun protection Factor 6) was blended with 2877 gr of methylene chloride and 35 gr of CTA dissolved in a further 465 gr of methylene chloride. The resulting lacquers were mixed and spray dried under the conditions described in Example 2. The resulting powder was dermatologically tested for efficacy against 100 gr of the commercial blend alone and was found to be equally effective when 117.8 mg of product (100 mg active) was applied to the skin. The powder form blended into the skin very easily, had none of the disadvantages associated with sun oil, and remained on the skin for a considerable period of time.

EXAMPLE 4

201.1 gr of commercial suntan oil (sun protection factor 4) and 2877 gr of methylene chloride were mixed—35 gr of CTA was dissolved in a further 465 gr of methylene chloride. Both solutions were mixed, and the resultant lacquer spray dried under the conditions described in Example 2.

Efficacy tests on 100 mg of the commercial oil and 117.6 mg of powder (100 mg active) gave readings of true SPF values at 3.7 and 4.1, respectively.

It will be understood that the above description describes only several embodiments of the present invention and that other embodiments are within the spirit and scope of the present invention. Hence, the above description is provided by way of illustration and not by way of limitation. The invention is further defined as set forth in the claims.

What is claimed is:

1. A sunscreen composition for the delivery of a topical sunscreen, the composition comprising a formulation of a frangible, liquid-containing, cellulosic powder formed by spray evaporation and having particles ranging in average diameter from about one to about 500 micrometers, the particles further characterized by being microporous with a plurality of interconnecting pores ranging in size from about one to about 500 nanometers; and a liquid sunscreen preparation loaded within the pores of the powder particles, such that the liquid-containing powder has a liquid content ranging from about 50 percent to about 95 percent by weight and, upon application and rubbing, the rubbed powder breaks up and the sunscreen preparation is readily released.

2. The composition of claim 1 wherein the cellulosic powder is a polymeric powder chosen from the group consisting of cellulose acetates, cellulose butyrates, cellulose nitrates, cellulose propionates, ethyl celluloses, and discrete and molecular mixtures thereof.

3. The composition of claim 1 wherein the sunscreen preparation comprises a sunscreen compound chosen from the group consisting of oxybenzone, amyl-p-dimethylaminobenzoate, homomethyl salicylate, octyl salicylate, mono-p-aminobenzoate, octyl-methoxycinnamate, 2-ethoxy ethyl-p-methoxycinnamate, derivatives and mixtures thereof.

4. The composition of claim 1 wherein the composition further comprises a liquid carrier in which the frangible powder is incorporated.

5. The composition of claim 1 wherein the composition further comprises a binder in which the frangible powder is incorporated to form a stick.

6. The composition of claim 1 wherein the frangible powder is compacted into a cake.

* * * * *

UNITED STATES PATENT AND TRADEMARK OFFICE
CERTIFICATE OF CORRECTION

PATENT NO. : 5,209,923
DATED : May 11, 1993
INVENTOR(S) : Larry D. Nichols

It is certified that error appears in the above-indentified patent and that said Letters Patent is hereby corrected as shown below:

On the title page, Item [73]: Assignee reads:

--PUREPAC, INC., Elizabeth, N.J.--

Signed and Sealed this

First Day of March, 1994

Attest:

BRUCE LEHMAN

Attesting Officer

Commissioner of Patents and Trademarks